(12) United States Patent
West et al.

(10) Patent No.: US 7,371,419 B1
(45) Date of Patent: May 13, 2008

(54) METHOD OF ENRICHING GLUCORAPHANIN IN RADISH SEED PREPARATIONS

(75) Inventors: Leslie G. West, Glencoe, IL (US); Nam-Cheol Kim, Deerfield, IL (US); George W. Haas, Mount Prospect, IL (US); Nathan V. Matusheski, Gurnee, IL (US)

(73) Assignee: Kraft Foods Holdings, Inc., Northfield, IL (US)

( * ) Notice: Subject to any disclaimer, the term of this patent is extended or adjusted under 35 U.S.C. 154(b) by 0 days.

(21) Appl. No.: 11/617,934

(22) Filed: Dec. 29, 2006

(51) Int. Cl.
*A61K 36/00* (2006.01)
(52) U.S. Cl. ........................ 424/776; 424/725
(58) Field of Classification Search ................. 424/776
See application file for complete search history.

(56) References Cited

U.S. PATENT DOCUMENTS 6,242,018 B1 * 6/2001 Fahey et al. ................... 426/49
2003/0091518 A1 * 5/2003 Pauly et al. .................... 424/59

FOREIGN PATENT DOCUMENTS

JP 2005206495 DWPI * 8/2005

* cited by examiner

*Primary Examiner*—Christopher R Tate
*Assistant Examiner*—Randall Winston
(74) *Attorney, Agent, or Firm*—Fitch, Even, Tabin & Flannery

(57) ABSTRACT

The present invention relates to chemoprotective compounds and a method for producing chemoprotectant precursor-enriched extracts from crucifer seeds. More particularly, a method is provided for producing chemoprotectant precursor-enriched extracts from radish seeds with increased ratio of glucoraphanin to glucoraphenin. The general method comprises preparing an aqueous extract, contacting the aqueous extract with an adsorbent, removing the adsorbent to obtain a glucosinolate-containing extract, drying the glucosinolate-containing extract to obtain a dried glucosinolate-containing extract, mixing at least a portion of the dried glucosinolate-containing extract with a solvent to form a glucosinolate-containing suspension, clarifying the glucosinolate-containing suspension, contacting the glucosinolate-containing suspension with a catalyst, and introducing hydrogen for a time sufficient to obtain a chemoprotectant precursor-enriched extract. The chemoprotectant precursor-enriched extracts may be further processed to form a chemoprotectant precursor-enriched isolate or processed for use in various applications, including incorporation into a variety of food products and pharmaceuticals.

23 Claims, 2 Drawing Sheets

METHOD OF ENRICHING GLUCORAPHANIN IN RADISH SEED PREPARATIONS

The present invention relates to chemoprotective precursor compounds and a method for producing crucifer seed extracts enriched with chemoprotective precursor compounds which may be incorporated into a variety of food products, pharmaceuticals, and health supplements. More specifically, a hydrogenation method is provided that is effective for providing an extract having increased ratio of glucoraphanin to glucoraphenin in radish seed extracts.

BACKGROUND

It is generally agreed that diet plays a large role in controlling the risk of developing cancers and that increased consumption of fruits and vegetables may reduce cancer incidences in humans. The presence of certain minor chemical components in plants may provide a major protection mechanism when delivered to mammalian cells. Moreover, providing pharmaceuticals, nutritional supplements, or foods fortified or supplemented with cancer-fighting chemical components derived from plants may provide additional health benefits. An important trend in the U.S. food industry is to promote health conscious food products.

Cruciferous vegetables contain phytochemical precursors to potent chemoprotectants, especially glucoraphanin (which is also known as sulforaphane glucosinolate or 4-methylsulfinylbutyl glucosinolate) and its associated conversion product sulforaphane, that appear to trigger carcinogen detoxification mechanisms when delivered to mammalian cells. Glucosinolates are found in dicotyledenous plants and most commonly in the Brassicaceae (Cruciferae) families. Glucosinolates are sulfur-containing compounds of the general structure:

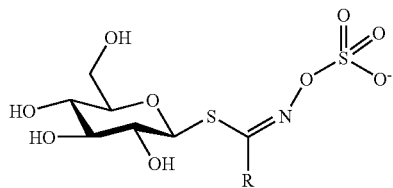

Glucosinolates include an R-group derived from amino acids and a thioglucosidic link to the carbon of a sulphonated oxime. The thioglucosidic bonds of the glucosinolates are hydrolyzed by beta-thioglucosidases into unstable glucosinolate aglycones, which undergo spontaneous rearrangement into chemoprotectant isothiocyanates, such as sulforaphane, and other compounds, such as nitriles and thiocyanates.

In addition to reducing the risk of certain cancers, glucoraphanin, through its bioactive conversion product sulforaphane, has recently been shown effective in destroying organisms responsible for causing the majority of stomach ulcers and may provide novel approaches for reducing the risk of developing cardiovascular and ocular diseases. Efforts are being undertaken to gain approval for making label claims on food products either naturally high in these agents or for foods containing added crucifer chemoprotectants. Products containing chemoprotectant additives, although without such label claims, are already on the market.

Cruciferous vegetables also contain other compounds, such as indole glucosinolates (for example, 4-hydroxyglucobrassican), which may be problematic for maintaining good health. Not only are these compounds weak inducers of the carcinogen detoxification system, but they can also induce systems which may bioactivate certain pro-carcinogens. Therefore, it is advantageous to produce glucoraphanin-containing preparations containing as little residual indole glucosinolates, or other adverse compounds, as possible.

The production of glucosinolates, particularly glucoraphanin, is problematic because of their high cost. Until the present invention, the best production source of glucoraphanin was expensive specialty broccoli cultivars. The considerable health potential of glucosinolates has not been realized due to the high cost of sourcing glucoraphanin. Hence, there is a need to provide alternative methods for producing high yields of glucosinolates, particularly glucoraphanin.

The present process, which is both technically straightforward and attractive from a production cost standpoint, provides such improvements. Indeed, the present process makes it possible to prepare extracts enriched with chemoprotectant precursor compounds, particularly glucoraphanin, from relatively inexpensive radish seeds while offering the health benefits of extracts prepared from substantially more expensive broccoli cultivars.

SUMMARY

The present invention is directed to crucifer seed extracts, particularly radish seed extracts, enriched with chemoprotectant precursor compositions, and methods for their preparation. Treatment of aqueous extracts from crucifer seeds, preferably radish seeds, with the method of the invention substantially increases the amount of certain chemoprotectant precursor compounds (alkyl glucosinolates), such as glucoraphanin. The method provides a crucifer seed extract enriched with chemoprotectant precursors by converting glucoraphenin, a compound found in radish seeds, to glucoraphanin. Glucoraphenin, although it has a similar chemical structure to that of glucoraphanin, is not believed to have similar health promoting activities. The structures of glucoraphanin and glucoraphenin are shown below:

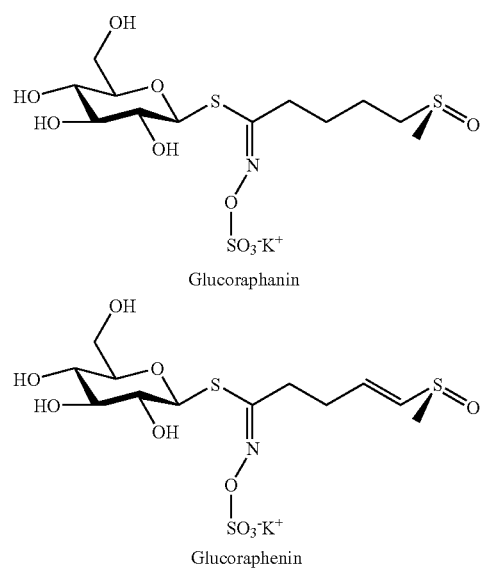

The method of the invention converts glucoraphenin to glucoraphanin via hydrogenation reactions (generally including one, two, or three hydrogenation steps, although additional hydrogenation steps may be used if needed). Generally, the crucifer seed extract produced by the method of the invention has a ratio of glucoraphanin to glucoraphenin of at least about 1:1, preferably at least about 5:1, even more preferably at least about 100:1, and most preferably glucoraphenin is no longer detectable by HPLC. The resulting extract may be dried or used directly as an additive in a variety of foodstuffs, health supplements, or pharmaceutical compositions.

A method is provided for enriching chemoprotectant precursors from crucifer seeds, such as radish seeds. Seeds from crucifer vegetables have been identified as a good source of chemoprotectant precursor phytochemicals. Members of the crucifer family which are especially useful include broccoli, kale, collard, curly kale, marrowstem kale, thousand head kale, Chinese kale, cauliflower, Portuguese kale, brussel sprouts, kohlrabi, Jersey kale, savoy cabbage, collards, borecole, radish, and the like, as well as mixtures thereof. In a preferred aspect, radish seeds are utilized. Generally, radish sprouts are not a useful source of chemoprotectant precursors because, as the seeds sprout, glucoraphenin in converted to 4-methylthio-3-butenyl glucosinolate, which is not a chemoprotectant precursor.

Generally, the method includes preparing an aqueous extract of crucifer seeds. Optionally, the aqueous extract may be separated from cellular materials. The aqueous extract is contacted with adsorbents to remove certain compounds that are problematic for good health, namely certain indole glucosinolates as well as undesirable flavors, odors, and colors. Adsorbents which may be utilized include activated carbon, silica, a variety of chemically-modified silicas (such as C18 silica), bleaching clay, and the like, as well as mixtures thereof. Preferably, the adsorbent is activated carbon. Generally, about 1 to about 20 percent by weight adsorbent based on dry weight of seed material is mixed with the aqueous extract. In a preferred aspect, about 8 to about 12 weight percent by weight adsorbent based on dry weight of seed material is mixed with the aqueous extract. In another aspect, the aqueous extract may be run through a column containing adsorbent.

The aqueous extract is separated from the adsorbent to provide a glucosinolate-containing extract using conventional techniques (e.g., filtration, decanting, centrifugation, and the like). The glucosinolate-containing extract is then dried to form a dried glucosinolate-containing extract. The dried glucosinolate-containing extract is then suspended in a solvent to form a glucosinolate-containing suspension.

The suspension may be clarified before hydrogenation if desired. Low pressure or high pressure hydrogenation may be used to convert glucoraphenin to glucoraphanin. A catalyst is added to the glucosinolate-containing suspension and the hydrogenation reaction is generally conducted in a one, two, or three step hydrogenation reaction (although additional hydrogenation steps may be used if needed), depending on the desired ratio of glucoraphanin to glucoraphenin in the resulting product. Suitable catalysts include palladium, platinum, nickel, any derivatives thereof, and the like. Generally, hydrogenation is conducted at a temperature of about 25° C. to about 450° C. and hydrogen is introduced at a pressure of about 50 to about 10,000 psi. The reaction product is filtered between hydrogenation reactions to remove spent catalyst and additional catalyst is added before each reaction. Generally, the method is effective for providing a chemoprotectant precursor-enriched extract having a ratio of glucoraphanin to glucoraphenin of about 1:1, preferably about 5:1, even more preferably at least about 100:1, and most preferably glucoraphenin is undetectable by HPLC.

In another aspect, food products and pharmaceuticals are provided that include the chemoprotectant precursor-enriched crucifer seed extract. The chemoprotectant precursor-enriched crucifer seed extract may be incorporated directly into food products or dried, cooled, frozen, or freeze-dried and then incorporated into the food products. Food product into which the chemoprotectant precursor-enriched extract may be incorporated include food supplements, drinks, shakes, baked goods, teas, soups, cereals, pills, tablets, salads, sandwiches, granolas, salad dressings, sauces, coffee, cheeses, yogurts, energy bars, and the like as well as mixtures thereof. Supplements include dietary supplements, nutritional supplements, herbal supplements, and the like. In this aspect, the food product may contain an effective amount of chemoprotectant precursor-enriched extract, such as about 1 to about 100 mg per single serving of the food product. An effective amount of the chemoprotectant precursor-enriched extract may also be incorporated into pharmaceutical compositions, such as about 10 to about 50 mg per single dosage.

DETAILED DESCRIPTION

The method of the present invention provides for cost effective enrichment of chemoprotectant precursors in crucifer seed extracts. More specifically, the present invention provides a method for converting glucoraphenin, a compound present in crucifer seeds, especially radish seeds, to the chemoprotectant precursor glucoraphanin.

As used herein, "chemoprotectants" and "chemoprotective compounds" refer to agents of plant origin that are effective for reducing the susceptibility of mammals to the toxic and neoplastic effects of carcinogens. Chemoprotectant "precursors" refer to agents which give rise to chemoprotectants by enzymatic and/or chemical means. Talalay, P. et al., *J. Nutr.*, 131 (11 Supp.): 30275-30335 (2001). Examples of such chemoprotectant precursors include alkyl glucosinolates, such as glucoraphanin.

Figure 1:
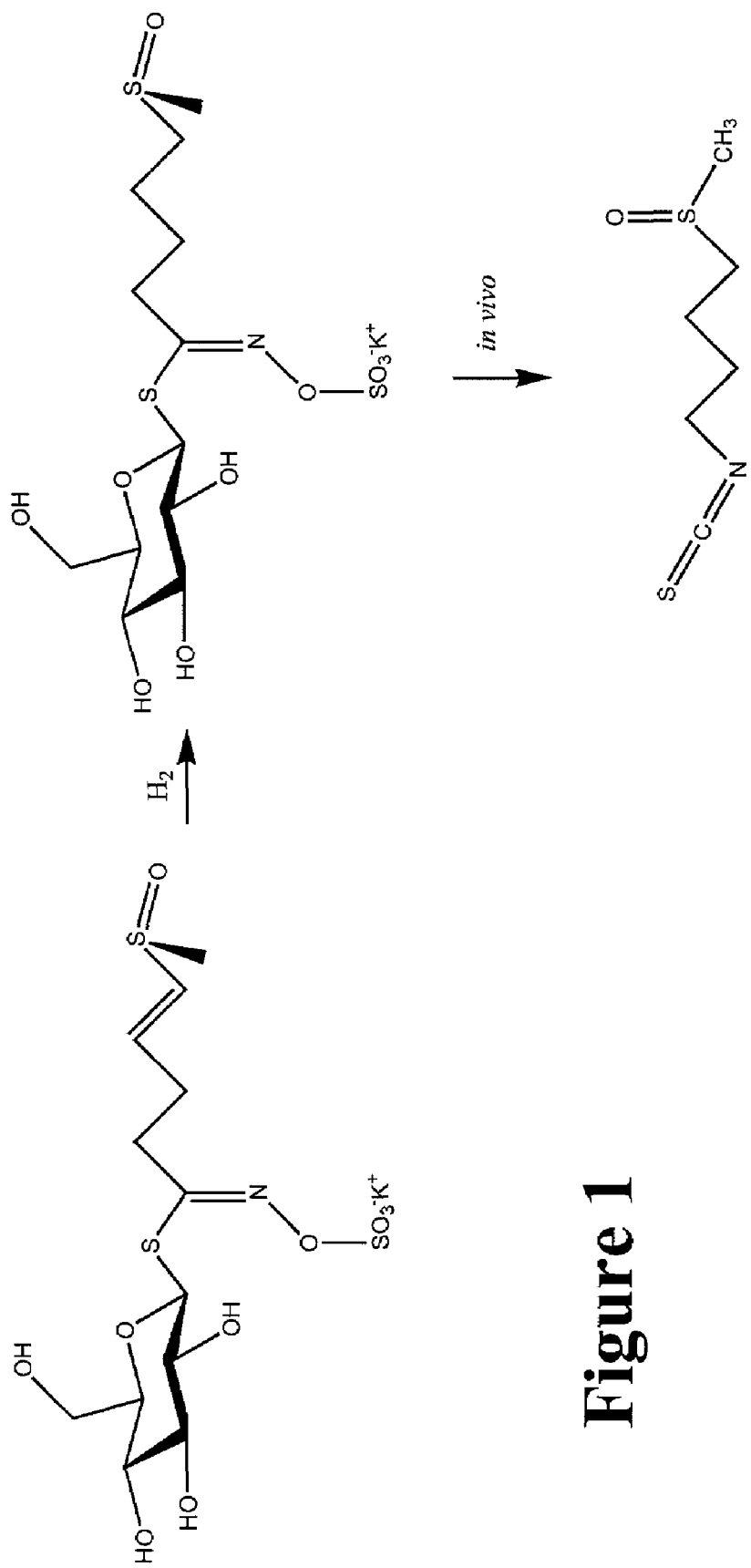
FIG. 1 provides the principal reactions for conversion of glucoraphenin to sulforaphane.

The principal reactions are illustrated in FIG. 1. The methods of the invention convert glucoraphenin to glucoraphanin via hydrogenation reactions. Then in vivo, the thioglucosidic bonds of glucoraphanin are hydrolyzed by gut microflora into unstable glucosinolate aglycones, which undergo spontaneous rearrangement into isothiocyanates, such as sulforaphane, and other compounds, such as nitrites and thiocyanates.

As used herein, "aqueous extract" means extracts prepared with 100 percent water or up to 25 percent addition of an organic solvent, such as ethyl alcohol.

As used herein, "effective amount" is an amount of additive which provides the desired effect or benefit upon consumption. Generally, about 1 to about 100 mg of the chemoprotectant enriched extract of the invention per single serving of the food product or about 1 to about 50 mg per single dosage of a pharmaceutical composition.

Crucifer seeds, particularly radish seeds, are useful starting materials. Generally, radish seeds contain greater amounts of glucoraphenin than other crucifer seeds. Radish seeds naturally contain a greater amount of glucoraphenin than glucoraphanin (generally with a ratio of glucoraphanin to glucoraphenin ranging from about 1:50 to about 1:150). Radish seeds naturally contain greater amounts of glucoraphenin than radish sprouts, which makes radish seeds more useful in the present invention. Barillari, J. et al., *J. Agric. Food Chem.*, 53: 9890-9896 (2005). Seeds are also easier to process and less expensive than mature plants.

Seeds suitable as sources of cancer chemoprotectants are generally cruciferous seeds from the family Brassicaceae. Preferably, the seeds are radish seeds. Particularly useful radish cultivars to be used in the claimed method are Cherry Belle and Champion. However, many other radish cultivars are suitable.

Figure 2:
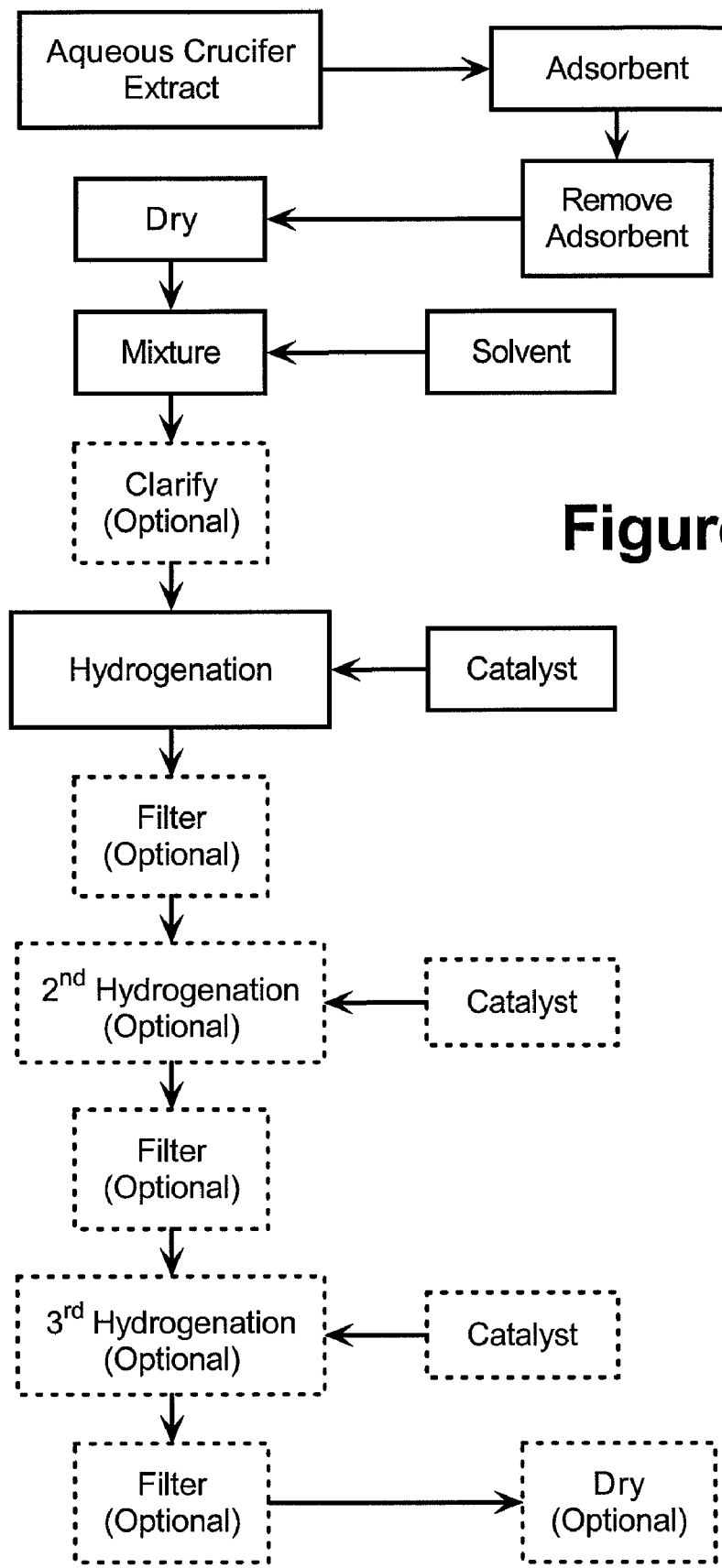
FIG. 2 provides a flowchart illustrating the general process of this invention.

One embodiment of the present invention is illustrated in FIG. 2. Generally, the method is carried out by treating crucifer seeds to produce an aqueous extract. Preferably, the treated seeds are pulverized and defatted crucifer seeds. In one aspect, the crucifer seeds may be defatted prior to forming an aqueous extract using known defatting procedures, such as described in West, L., *J. Agric. Food Chem.*, 52: 916-926 (2004), which is incorporated herein by reference. In another aspect, crucifer seeds may be ground, pulverized, or blended prior to addition of an aqueous solvent or simultaneously with the addition of an aqueous solvent.

The aqueous extract may be produced by any method known in the art. Generally, about 1 to about 5 parts of crucifer seeds, preferably radish seeds, are combined with about 5 to about 50 parts aqueous solvent and are maintained at about 90° C. to about 110° C., for about 5 to about 15 minutes, to form an aqueous crucifer seed extract. The aqueous solvent is preferably water but the aqueous solvent may also be an aqueous solvent containing an organic solvent, such as ethyl alcohol. Preferably, following extraction, residual seed material is removed from the aqueous crucifer seed extract, such as by filtration, centrifugation, decanting, or the like.

While adsorbent may be added in conjunction with the extraction of the seeds, it is preferred that the aqueous extract is treated with adsorbent in a separate step with heat treatment, preferably following removal of residual seed material. Generally, about 1 to about 20 percent by weight adsorbent based on dry weight of seed material is mixed with the aqueous crucifer seed extract, and heated to a temperature of about 90° C. to about 110° C. for about 5 to about 15 minutes. In a preferred aspect, about 8 to about 12 percent by weight adsorbent based on dry weight of seed material is mixed with the crucifer seed extract. In another aspect, the aqueous seed extract may be passed through a column containing an adsorbent, such as graphitized carbon black, to produce a glucosinolate-containing extract. Generally, the aqueous crucifer seed extract may be mixed directly with adsorbent in batch, semi-batch, semi-continuous, or continuous mode (e.g., using an adsorbent column). As used herein, adsorbents refer to compounds that are effective for preferentially adsorbing indole glucosinolates over alkyl glucosinolates. Treatment of the aqueous seed extract with adsorbents also serves to remove unwanted colors, odors, and flavors, and, importantly, removes significant amounts of indole glucosinolates. Useful adsorbents include activated carbon, silica, a variety of chemically-modified silicas (such as C18 silica), bleaching clay, and the like. Preferably, the adsorbent is activated carbon.

The aqueous extract may be centrifuged and/or filtered to remove spent adsorbent to form a clarified glucosinolate-containing extract. The adsorbent may be separated from the glucosinolate-containing extract by any means known in the art, such as by filtration, ultrafiltration, centrifugation, decanting, or the like. Following removal of the spent adsorbent, the glucosinolate-containing extract is then dried for a time sufficient to reduce the water content of the glucosinolate-containing extract to less than about 10 percent, preferable to less than about 5 percent, to form a dried glucosinolate-containing extract. Generally, the glucosinolate-containing extract may be dried using any known method, such as, but not limited to, freeze drying, spray drying, vacuum drying, and the like. The clarified glucosinolate-containing extract may then be additionally treated with ultrafiltration, if desired.

At least a portion of the dried glucosinolate-containing extract is then mixed with a solvent to form a glucosinolate-containing suspension. Suitable solvents include, for example, ethanol, methanol, water, or mixtures thereof. Generally, when low pressure hydrogenation conditions are used, the solvent should contain organic solvent, such as ethanol, methanol, or a mixture thereof, generally requiring at least about 50 percent organic solvent. Preferably, the solvent is ethanol. When high pressure hydrogenation conditions are used, an aqueous solvent alone can be used (although organic solvent could be included if desired). Generally, the amount of solvent added to the dried glucosinolate-containing extract is not critical as long as enough solvent is added to form a homogenous suspension. The solvent may be mixed or blended with the dried extract by any means known in the art, such as by sonication, shaking, microwaving, or the like, to form a substantially homogenous glucosinolate-containing suspension.

Although optional, it is preferable to remove insolubles in the glucosinolate-containing suspension following the mixing step. The insolubles can be separated from the glucosinolate-containing suspension by any conventional technique, including, for example, filtration, centrifugation, decanting, or the like, to form a clarified glucosinolate solution. Preferably, the insolubles are separated by filtration using a 0.45 micron pore size filter.

Generally, hydrogenation may be carried out at a temperature of about 25° C. to about 450° C. and using relatively low hydrogenation pressures, such as about 10 to about 100 psi, or under relatively high hydrogenation pressures, such as 1000 to about 10,000 psi. The hydrogenation reaction may be carried out in a continuous, semi-continuous, batch, or semi-batch process. In a hydrogenation vessel, such as a low pressure hydrogenation apparatus (Parr Hydrogenator Series 3916, Parr Instrument Co., Moline, Ill.), the glucosinolate-containing suspension is contacted with a catalyst and hydrogen is introduced at a pressure of about 10 to about 100 psi, preferably about 50 to about 80 psi, and at a temperature in the range of from about 25° C. to about 100° C., preferably about 25° C. to about 50° C., for a time sufficient to obtain a chemoprotectant precursor-enriched extract having a ratio of glucoraphanin to glucoraphenin of at least about 1:1. Hydrogenation is generally carried out for about 10 to about 24 hours under mild shaking, although high pressure hydrogenation may be carried out for less time, such as for about 5 to about 12 hours.

A variety of conventional catalysts may be employed, such as, but not limited to, nickel, palladium, or platinum catalysts. Preferably, the catalyst is a platinum catalyst, such as platinum (IV) oxide from Sigma-Aldrich Corp. (Milwaukee, Wis.). The catalyst is generally used in an amount in the range of about 1 to about 25 percent and preferably in the range of about 5 to about 20 percent.

Following hydrogenation, the reaction product is clarified to remove spent catalyst, such as by filtration, ultrafiltration, decanting, centrifugation, or the like. Generally, the reaction product has a ratio of glucoraphanin to glucoraphenin of at least about 1 to 1, although one of skill in the art will recognize that the ratio of glucoraphanin to glucoraphenin after hydrogenation is impacted by the ratio of glucoraphanin to glucoraphenin in the starting crucifer seeds.

Depending on the desired ratio of glucoraphanin to glucoraphenin in the final product, the product from the first hydrogenation step may be optionally subjected to further hydrogenation in a second hydrogenation step to increase the ratio of glucoraphanin to glucoraphenin. The second hydrogenation step is carried out by adding catalyst, generally about 1 to about 25 percent, preferably about 5 to about 20 percent, to the filtered product from the first hydrogenation step. The second hydrogenation step is carried out for an additional 10 to about 24 hours under shaking at a temperature of about 25 to about 100° C. Generally, the reaction occurs for a time sufficient to obtain a chemoprotectant precursor-enriched extract having a ratio of glucoraphanin to glucoraphenin of at least about 5 to 1, preferably 10 to 1. Following the second hydrogenation reaction, the reaction product is clarified to remove spent catalyst, such as by filtration, ultrafiltration, decanting, centrifugation, or the like.

Again, depending on the desired ratio of glucoraphanin to glucoraphenin, the product from the second hydrogenation reaction may be optionally subjected to a third hydrogenation step to further increase the ratio of glucoraphanin to glucoraphenin. The second hydrogenation step is carried out by adding catalyst, generally about 1 to about 25 percent, preferably about 5 to about 20 percent, to the product from the first hydrogenation reaction. The second hydrogenation step is carried out for an additional 10 hours to about 24 hours under shaking at a temperature of about 25 to about 100° C. Generally, the reaction occurs for a time sufficient to obtain a chemoprotectant precursor-enriched extract having a ratio of glucoraphanin to glucoraphenin of at least about 100 to 1, preferably such that glucoraphenin is no longer detectable by HPLC.

Generally, only three hydrogenation steps using a low pressure hydrogenation apparatus are necessary to convert substantially all of the glucoraphenin to glucoraphanin, such that glucoraphenin is no longer detectable by HPLC, although additional hydrogenation steps may be used if desired. When using low pressure hydrogenation, it is preferred to use at least two hydrogenation steps with the conditions described above instead of increasing the amount of catalyst in a single hydrogenation step. Generally, more undesired side reactions occur when greater amounts of catalyst are added. Also, increasing the reaction time in a single hydrogenation step generally does not substantially increase the ratio of glucoraphanin to glucoraphenin in the product because the catalyst becomes poisoned. When using high pressure hydrogenation, generally fewer hydrogenation steps are required to obtain the desired ratio of glucoraphanin to glucoraphenin, although of course additional hydrogenation steps may be used if necessary.

Following the third hydrogenation reaction, the reaction product may be clarified, such as by filtration, ultrafiltration, decanting, centrifugation, or the like, to remove spent catalyst and to obtain the chemoprotectant precursor-enriched extract. Preferably, ultrafiltration using a 0.45 micrometer pore size filter is used and the chemoprotectant precursor-enriched extract is collected as the filtrate.

The at least one step hydrogenation process can be run in a batch, semi-batch, semi-continuous, or continuous mode. Preferably, the process is carried out in continuous mode.

The chemoprotectant precursor-enriched extracts of the invention may be further processed into a variety of forms. For example, the chemoprotectant precursor-enriched extract may be dried, such as by spray drying, freeze drying, vacuum drying, or the like, to form a dried chemoprotectant precursor-enriched extract. The chemoprotectant precursor-enriched extract may also be further processed by cooling or freezing, or may be subjected to membrane processing, chromatographic processing, or dialysis to remove high molecular weight compounds such as proteins and polysaccharides, or the like, such as to form a chemoprotectant precursor isolate or purified product.

The chemoprotectant precursor-enriched extract may also have introduced optional ingredients or components, such as, for example, flavorants, nutrients, vitamins, colorants, nutraceutical additives, antioxidants, probiotics, and the like, so long as the optional ingredients do not adversely affect the stability in a significant manner. In particular, the presence and amount of such optional ingredients can, of course, vary considerably depending on the product in which the extract is incorporated.

The chemoprotectant precursor-enriched extract of the invention may be included in a variety of products, including food products and pharmaceuticals. The chemoprotectant precursor-enriched crucifer seed extract may also be used as a food fortificant. Food product into which the extract may be incorporated include food supplements, drinks, shakes, baked goods, teas, soups, cereals, pills, tablets, salads, sandwiches, granolas, salad dressings, sauces, coffee, cheeses, yogurts, energy bars, and the like as well as mixtures thereof. Supplements include dietary supplements, nutritional supplements, herbal supplements, or the like. In this aspect, the food product may contain an effective amount of chemoprotectant precursor-enriched extract, such as about 1 to about 100 mg per single serving of the food product. An effective amount of the chemoprotectant precursor-enriched extract may also be incorporated into pharmaceutical compositions, such as about 10 to about 50 mg.

The following examples are intended to illustrate the invention and not to limit it. Unless otherwise stated, all percentages, parts, and ratios are by weight. All references (including publications, patents, patent applications, patent publications, and the like) cited in the present specification are hereby incorporated by reference.

EXAMPLES

Example 1

First (or Single) Hydrogenation Step

Radish seeds (Diakon) (obtained from New England Seed Co., Hartford, Conn.) were pulverized in argon using a high-speed blender (Model 500, Vita-Mix Corp., Cleveland, Ohio). Hexane-extractable lipids were removed via Soxhlet extraction using hexane (Sigma-Aldrich, Milwaukee, Wis.) and residual solvent was minimized under high vacuum. The seed material was stirred into boiling water (100 g seed material per liter of water) and held for 10 minutes. The mixture was filtered hot through Whatman #2 filter paper. Activated charcoal (DARCO® G-60 from Sigma-Aldrich, Milwaukee, Wis.) was added at 10 g activated charcoal per 100 g seed material), and the mixture was brought just to boiling. When cooled to room temperature, the charcoal was removed by centrifugation (about 7000×G for 30 minutes) and the supernatant was filtered through Nylon membranes (0.45 micron followed by 0.2 micron) to obtain a clarified extract. The clarified extract was ultrafiltered using a 3000 MWCO tangential flow device (Ultrasette™, Pall Corp., East Hills, N.Y.) operated at filtrate and recirculation flow rates of about 2 ml/min and about 200 ml/min, respectively.

Filtrates were freeze-dried and analyzed for glucoraphenin using HPLC as described in West et al., *J. Chromatography A*, 966: 227-232 (2002), which is incorporated herein by reference, using a YMC ODS-A C18 column (150×4.6 mm i.d., 5 micrometer particle size from Waters Co., Milford, M.A.). Typically, 200 g of seeds were processed at one time yielding >20 g of semi-purified extract containing >25 percent glucoraphenin. The starting ratio of glucoraphanin to glucoraphenin was found to be about 1:90 using HPLC.

One-half gram of the dried glucosinolate-containing extract was suspended in 150 ml absolute ethanol and sonicated for ten minutes. Insolubles were separated by filtration using a 0.45 micron Nylon filter and the filtrate collected. The filtrate was transferred to a 250 ml hydrogenation reaction bottle and 100 mg of platinum (IV) oxide from Sigma-Aldrich, Milwaukee, Wis., was added. The reaction mixture was connected to a low-pressure hydrogenation apparatus (Parr Hydrogenator Series 3916, Parr Instrument Company, Moline, Ill.) and hydrogen was introduced at a pressure of 60 psi. After 18 hours of continuous mild shaking at room temperature, the reaction bottle was disconnected and the solution was filtered using a 0.45 micron Nylon filter to remove spent catalyst. The filtrate was collected and analyzed by HPLC, which revealed a significant increase in the ratio of glucoraphanin to glucoraphenin from the initial ratio of 1:90 in the initial crucifer seed extract to a ratio of about 2:1 after hydrogenation.

Example 2

Second Hydrogenation Step

The experiment of Example 1 was repeated except that after the initial reaction step, an additional 100 mg of platinum (IV) oxide was added to the filtered reaction mixture of Example 1 and the hydrogenation reaction continued for approximately 24 hours. The reaction bottle was disconnected and the solution was filtered using a 0.45 micron nylon filter to remove spent catalyst. The filtrate was collected and analyzed by HPLC, which revealed another increase in the ratio of glucoraphanin to glucoraphenin to about 10:1.

Example 3

Third Hydrogenation Step

The experiment of Example 2 was repeated. 100 mg of platinum (IV) oxide was added to the filtered reaction mixture of Example 2 and the hydrogenation reaction was continued for approximately eighteen hours. The reaction bottle was disconnected and the solution was filtered using a 0.45 micron nylon filter to remove spent catalyst. The filtrate was collected and analyzed by HPLC, which revealed another substantial increase in glucoraphanin content such that glucoraphenin was no longer detectable by HPLC, which indicates that the hydrogenation reaction had proceeded essentially to completion.

While the invention has been described in terms of preferred embodiments, those skilled in the art will recognize that the invention can be practiced with modification within the spirit and scope of the appended claims.

What is claimed is:

1. A method for enriching chemoprotectant precursors in crucifer seed preparations comprising:
    (i) preparing an aqueous extract from crucifer seeds that contain glucosinolate;
    (ii) contacting the aqueous extract with an adsorbent;
    (iii) removing the adsorbent from the aqueous extract to obtain a glucosinolate-containing extract;
    (iv) drying the glucosinolate-containing extract to obtain a dried glucosinolate-containing extract;
    (v) mixing at least a portion of the dried glucosinolate-containing extract with a solvent to form a glucosinolate-containing suspension;
    (vi) optionally removing insoluble materials to form a clarified glucosinolate-containing suspension;
    (vii) contacting the glucosinolate-containing suspension from either (v) or (vi) with a catalyst;
    (viii) introducing hydrogen at a temperature of about 25° C. to about 450° C. and a pressure of about 10 to about 10,000 psi for a time sufficient to obtain a chemoprotectant precursor-enriched extract.

2. The method of claim 1, further comprising filtering the chemoprotectant precursor-enriched extract of (viii) to form a clarified chemoprotectant precursor-enriched extract.

3. The method of claim 1, wherein hydrogen is introduced at a temperature of about 25 to about 100° C. and a pressure of about 10 to about 100 psi for a time sufficient to obtain a chemoprotectant precursor-enriched extract.

4. The method of claim 2, further comprising drying the clarified chemoprotectant precursor-enriched extract to form a dried chemoprotectant precursor-enriched extract.

5. The method of claim 1, wherein the chemoprotectant precursor is glucoraphanin.

6. The method of claim 1, wherein the chemoprotectant precursor-enriched extract has a ratio of glucoraphanin to glucoraphenin of at least about 1 to 1.

7. The method of claim 1, wherein the glucosinolate-containing suspension is contacted with a catalyst in an amount of about 1 to about 25 weight percent.

8. The method of claim 1, wherein the catalyst is selected from the group consisting of platinum, palladium, nickel, derivatives thereof, and mixtures thereof.

9. The method of claim 1, wherein the aqueous extract of crucifer seed is formed by contacting the crucifer seeds with water having a temperature of about 90° C. to about 110° C. for at least about 10 minutes.

10. The method of claim 1, wherein the crucifer seed is radish seed.

11. The method of claim 1, wherein the adsorbent is selected from the group consisting of activated carbon, silica, various chemically-modified silicas, bleaching clay, and mixtures thereof.

12. The method of claim 11, wherein the adsorbent is activated carbon.

13. The method of claim 1, wherein about 1 to about 20 percent adsorbent is mixed with the aqueous extract.

14. The method of claim 1, wherein the solvent is ethanol.

15. The method of claim 1, wherein hydrogen is introduced for about 1 to about 24 hours.

16. The method of claim 1, further comprising a second hydrogenation step, wherein the chemoprotectant precursor-enriched extract of the first hydrogenation step is contacted with a catalyst in an amount of about 1 to about 25 percent and hydrogen is introduced at a temperature of about 25° C. to about 450° C. and a pressure of about 10 to about 10,000 psi for a time sufficient to obtain a chemoprotectant precursor-enriched extract.

17. The method of claim 16, wherein hydrogen is introduced at a temperature of about 25 to about 100° C. and a pressure of about 10 to about 100 psi for a time sufficient to obtain a chemoprotectant precursor-enriched extract.

18. The method of claim 16, wherein the chemoprotectant precursor-enriched extract of the second hydrogenation step has a ratio of glucoraphanin to glucoraphenin of at least about 5 to 1.

19. The method of claim 16, further comprising a third hydrogenation step, wherein the chemoprotectant precursor-enriched extract of the second hydrogenation step is contacted with a catalyst in an amount of about 1 to about 25 percent and hydrogen is introduced at a temperature of about 25° C. to about 450° C. and a pressure of about 10 to about 10,000 psi for a time sufficient to obtain a chemoprotectant precursor-enriched extract.

20. The method of claim 19, wherein hydrogen is introduced at a temperature of about 25 to about 100° C. and a pressure of about 10 to about 100 psi for a time sufficient to obtain a chemoprotectant precursor-enriched extract.

21. The method of claim 19, wherein the chemoprotectant precursor-enriched extract of the third hydrogenation step has a ratio of glucoraphanin to glucoraphenin of at least about 100 to 1.

22. The method of claim 19, wherein glucoraphenin is not detectable by HPLC in the chemoprotectant precursor-enriched extract.

23. The method of claim 1 wherein the crucifer seed is a seed selected from the group consisting of broccoli, kale, collard, curly kale, marrowstem kale, thousand head kale, Chinese kale, cauliflower, Portuguese kale, brussel sprouts, kohlrabi, Jersey kale, savoy cabbage, collards, borecole, radish, and mixtures thereof.

* * * * *